(12) United States Patent
Nakajima

(10) Patent No.: US 9,551,097 B2
(45) Date of Patent: Jan. 24, 2017

(54) DEVICE FOR PRODUCING ABSORBENT BODY

(71) Applicant: Zuiko Corporation, Osaka (JP)

(72) Inventor: Yoshihiro Nakajima, Osaka (JP)

(73) Assignee: Zuiko Corporation, Osaka (JP)

( * ) Notice: Subject to any disclaimer, the term of this patent is extended or adjusted under 35 U.S.C. 154(b) by 0 days.

(21) Appl. No.: 14/413,627

(22) PCT Filed: Jun. 27, 2013

(86) PCT No.: PCT/JP2013/067628
§ 371 (c)(1),
(2) Date: Jan. 8, 2015

(87) PCT Pub. No.: WO2014/010427
PCT Pub. Date: Jan. 16, 2014

(65) Prior Publication Data
US 2015/0167213 A1    Jun. 18, 2015

(30) Foreign Application Priority Data

Jul. 10, 2012 (JP) .................................. 2012-154346

(51) Int. Cl.
*D04H 1/70* (2012.01)
*A61F 13/49* (2006.01)
(Continued)

(52) U.S. Cl.
CPC ........... *D04H 1/70* (2013.01); *A61F 13/15617* (2013.01); *A61F 13/15658* (2013.01); *A61F 13/49* (2013.01); *D04H 1/732* (2013.01)

(58) Field of Classification Search
USPC .................. 425/DIG. 102; 428/85, 504, 584
See application file for complete search history.

(56) References Cited

U.S. PATENT DOCUMENTS 4,666,647 A * 5/1987 Enloe ................ A61F 13/15658
19/148
5,004,579 A 4/1991 Wislinski et al.
(Continued)

FOREIGN PATENT DOCUMENTS

CN    102361615 A    2/2012
EP    0399511 A2    11/1990
(Continued)

OTHER PUBLICATIONS

Office Action issued Feb. 10, 2015, in corresponding Japanese Patent Application No. 2012-154346 (with translation) (10 pages).
(Continued)

*Primary Examiner* — Alison L Hindenlang
*Assistant Examiner* — Kimberly A Stewart
(74) *Attorney, Agent, or Firm* — Osha Liang LLP

(57) ABSTRACT

A device for producing an absorbent body includes a rotating fiber stacking drum that includes an adsorbent molding section configured to mold fluff pulp into an absorbent body having a desired shape. The rotating fiber stacking drum further includes a cylinder having an outer circumference on which the adsorbent molding section is formed, and paired side walls that close ends of the cylinder, respectively. The device for producing an absorbent body further includes a sucking means, which is configured to generate an air flow from the outer circumference side of the adsorbent molding section toward the inside of the cylinder by sucking air in the rotating fiber stacking drum. The sucking means is connected to each of two side walls of the rotating fiber stacking drum.

2 Claims, 2 Drawing Sheets

(51) Int. Cl.
*D04H 1/732* (2012.01)
*A61F 13/15* (2006.01)

(56) References Cited

U.S. PATENT DOCUMENTS

| | | | |
|---|---|---|---|
| 5,064,484 A * | 11/1991 | Craig | A61F 13/15626 156/296 |
| 5,531,235 A | 7/1996 | Hassenboehler, Jr. | |
| 6,652,798 B1 * | 11/2003 | Edvardsson | A61F 13/15658 264/112 |
| 2010/0032858 A1 | 2/2010 | de Carvalho et al. | |
| 2011/0233828 A1 | 9/2011 | Yano | |
| 2012/0056357 A1 | 3/2012 | Suzuki | |

FOREIGN PATENT DOCUMENTS

| | | |
|---|---|---|
| JP | 3-76825 A | 4/1991 |
| JP | 4-57952 A | 2/1992 |
| JP | 4-200544 A | 7/1992 |
| JP | 6-4076 U | 1/1994 |
| JP | 8-502326 A | 3/1996 |
| JP | 8-337954 A | 12/1996 |
| JP | 2008-231609 A | 10/2008 |
| WO | 2010/058709 A1 | 5/2010 |
| WO | 2010/109988 A1 | 9/2010 |

OTHER PUBLICATIONS

Office Action issued Aug. 18, 2015, in corresponding Japanese Patent Application No. 2012-154346 (with translation) (7 pages).
International Preliminary Report on Patentability issued Jan. 13, 2015, in related International Patent Application No. PCT/JP2013/067628 (1page).
Written Opinion issued Jan. 10, 2015, in related International Patent Application No. PCT/JP2013/067628 (with translation) (12 pages).
International Search Report issued in PCT/JP2013/067628 mailed on Sep. 17, 2013 (4 pages).
Extended European Search Report issued in corresponding European Application No. 13816332.4 dated Mar. 2, 2016 (5 pages).
Office Action in counterpart Chinese Patent Application No. 2013800366365 issued Jun. 3, 2016 (10 pages).

* cited by examiner

DEVICE FOR PRODUCING ABSORBENT BODY

TECHNICAL FIELD

The present invention relates to a device for producing an absorbent body used for sanitary items such as paper diapers and sanitary napkins.

BACKGROUND ART

As described in Patent Literature 1, an absorbent body with a desired shape is formed in such a way that, a mixed flow is formed by carrying fluff pulp formed by crushing a pulp sheet on an air flow to a duct and at the same time supplying a water absorbing polymer in the duct to be merged with the fluff pulp carrying flow, and the mixed flow is then transported to a rotating fiber stacking drum so that the mixed flow is adsorbed and retained by an adsorbent molding section which is formed on the outer circumference of the rotating fiber stacking drum. The adsorption to the adsorbent molding section is performed in such a way that the air in the rotating fiber stacking drum is sucked by a sucking means connected to a side wall of the rotating fiber stacking drum to keep the inside of the rotating fiber stacking drum to be negative in pressure.

CITATION LIST

Patent Literature

[Patent Literature 1] Japanese Unexamined Patent Publication No. 8-337954

SUMMARY OF INVENTION

Technical Problem

The sucking means configured to suck the air in the rotating fiber stacking drum is typically connected to one of the two side walls of the rotating fiber stacking drum. For this reason, assuming that the axis direction of the rotating fiber stacking drum is a width direction, when a wide absorbent body is formed, the sucking force on the side of the side wall to which the sucking means is connected is relatively larger than the sucking force on the other side wall side. Because the sucking force is uneven in the width direction of the adsorbent molding section, the thickness of the absorbent body molded by the adsorbent molding section is disadvantageously uneven in the width direction.

One or more embodiments of the present invention provide a device for producing an absorbent body, which is capable of forming an absorbent body that is even in thickness in the width direction.

Solution to Problem

One or more embodiments of the device for producing an absorbent body include a rotating fiber stacking drum that includes an adsorbent molding section configured to mold fluff pulp into an absorbent body having a desired shape, the rotating fiber stacking drum including: a cylinder having an outer circumference on which the adsorbent molding section is formed; and paired side walls that close ends of the cylinder, respectively, sucking means, which is configured to generate an air flow from the outer circumference side of the adsorbent molding section toward the inside of the cylinder by sucking air in the rotating fiber stacking drum, being connected to each of two side walls of the rotating fiber stacking drum.

According to the arrangement above, because the air in the rotating fiber stacking drum is sucked by the sucking means connected to the respective two side walls of the rotating fiber stacking drum, a sucking force which is uniform in the width direction of the adsorbent molding section is exerted even when a wide absorbent body is formed. As a result, the thickness of the absorbent body molded by the adsorbent molding section is made uniform in the width direction. It is noted that the widths above indicate the sizes in the axis direction.

In addition to the above, in one or more embodiments of the device of the present invention, the paired side walls are arranged not to be rotatable, and the cylinder is arranged to be rotatable. According to this arrangement, because the paired side walls do not rotate with respect to the rotating cylinder, the sucking means is easily connectable to each of the paired side walls.

In addition to the above, one or more embodiments of the device of the present invention may be arranged to further include: supplying means which is connected to each of the side walls of the rotating fiber stacking drum to supply compressed air into the rotating fiber stacking drum; and a partition plate that partitions the inside of the rotating fiber stacking drum into a plurality of regions including a sucking region connected to the sucking means and a discharge region connected to the supplying means, in the discharge region, the compressed air being discharged from the inside of the cylinder toward the outer circumference side of the adsorbent molding section. According to this arrangement, from each of the supplying means connected to the respective side walls of the rotating fiber stacking drum, compressed air is supplied into the discharge region. The supplying means is typically connected to one side wall of the rotating fiber stacking drum. In this case, the pressing force on the side wall side where the supplying means is connected is relatively larger than the pressing force on the opposite side wall side in an attempt to take a wide absorbent body out from the adsorbent molding section by means of a pressing force of compressed air. As such, the pressing force is not uniform in the width direction of the adsorbent molding section, with the result that the absorbent body cannot be successfully taken out from the adsorbent molding section. In this regard, because the supplying means are connected to the respective side walls of the rotating fiber stacking drum to supply the compressed air into the discharge region therefrom, the pressing force is uniform in the width direction of the adsorbent molding section even if a wide absorbent body is formed. In this way, the absorbent body is successfully taken out from the adsorbent molding section.

Advantageous Effect of Invention

When one or more embodiments of the device for producing the absorbent body is used, the absorbent body molded by the adsorbent molding section is uniform in thickness in the width direction, because the sucking force is uniform in the width direction of the adsorbent molding section.

DESCRIPTION OF EMBODIMENT

The following will describe a preferred embodiment of the present invention with reference to figures.
(Structure of Device for Producing Absorbent Body)

Figure 1:
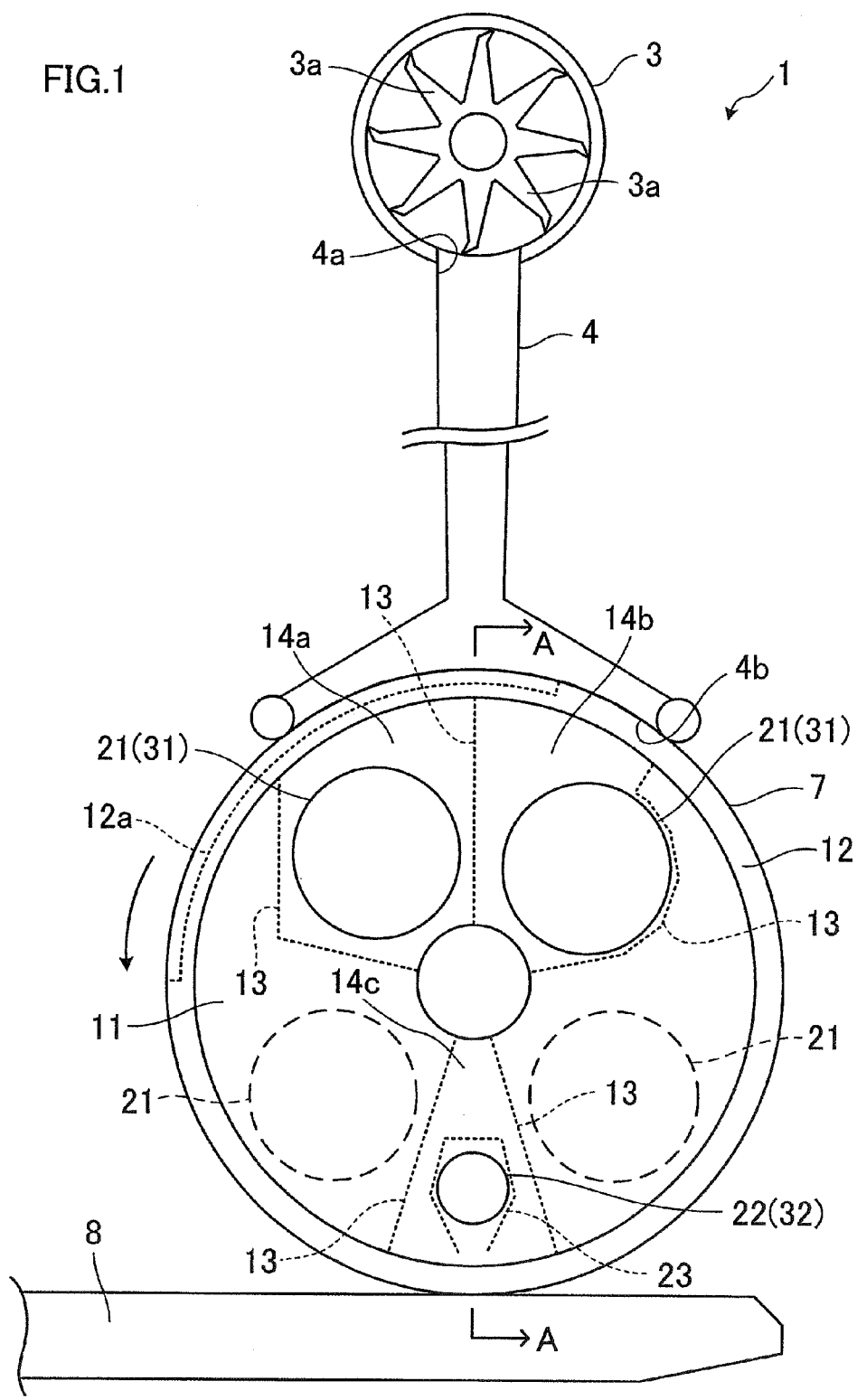
FIG. 1 is a schematic view of a device for producing an absorbent body.

As shown in FIG. 1, a device for producing absorbent body 1 of the present embodiment includes a crusher 3 which is configured to crush a material pulp sheet into fluff pulp, a duct 4 to which the fluff pulp is carried on an air flow (i.e., to which the fluff pulp is carried by air), a rotating fiber stacking drum 7 configured to mold the fluff pulp into an absorbent body with a desired shape, and a vacuum conveyor 8 configured to receive the absorbent body molded by the rotating fiber stacking drum 7.

The crusher 3 is attached to a one-end-side opening 4a of the duct 4. To the crusher 3, a pulp sheet is supplied from a pair of feed rollers (not illustrated). On the roll surface of the crusher 3, a plurality of rotating blades 3a are provided to finely crush the supplied pulp sheet. The fluff pulp formed by crushing the pulp sheet is, inside the duct 4, carried on an air flow generated in the duct 4, toward the rotating fiber stacking drum 7.

To a desired position between the ends of the duct 4, a water absorbing polymer supply pipe (not illustrated) is attached. Through this water absorbing polymer supply pipe, the water absorbing polymer is supplied into the duct 4. As the water absorbing polymer supplied to the duct 4 spreads inside the duct 4, a mixed flow in which the fluff pulp and the water absorbing polymer are evenly mixed is generated in the duct 4. This mixed flow is carried by air toward the rotating fiber stacking drum 7.

The rotating fiber stacking drum 7 includes a rotatable cylinder 12 and a pair of side walls 11 which are provided not to be rotatable and close the respective ends of the cylinder 12. The rotating fiber stacking drum 7 is pressed onto and connected to an other-end-side opening 4c of the duct 4 so that the cylinder 12 is rotatable. Each of the paired side walls 11 is connected to two suction ducts 21 and a single air supply duct 22. The numbers of the suction ducts 21 and the air supply duct 22 are not limited to the above, and the number of the suction ducts 21 may be three or more, for example.

On the outer circumference of the cylinder 12, an adsorbent molding section 12a is formed. This adsorbent molding section 12a corresponds to the shape of an absorbent body to be formed, allows air to pass therethrough, and is made of a metal mesh. As this adsorbent molding section 12a adsorbs and retains the mixed flow of the fluff pulp and the water absorbing polymer, an absorbent body with a desired shape is formed. The cylinder 12 is continuously rotated at a regular speed in the direction indicated by the arrow, by an unillustrated driving means.

The inside of the rotating fiber stacking drum 7 is partitioned by a plurality of partition plates 13 into a plurality of regions. More specifically, the inside of the rotating fiber stacking drum 7 is partitioned into two sucking regions 14a and 14b that are open upward and oppose the other-end-side opening 4c of the duct 4, a single discharge region 14c which is open downward and oppose the vacuum conveyor 8, and another region. The circumferential length of the sucking region 14a is half as long as the circumferential length of the other-end-side opening 4c. The circumferential length of the sucking region 14a is half as long as the circumferential length of the other-end-side opening 4c.

Each of the two neighboring sucking regions 14a and 14b is connected to one end of the suction duct 21 which has the other end that is connected to a sucking device 24 (shown in FIG. 2) such as a sucking fan. As the sucking device 24 sucks the air in the sucking region 14a through the suction duct 21, the pressure inside the sucking region 14a is kept to be negative. In a similar manner, as the sucking device 24 sucks the air in the sucking region 14b through the suction duct 21, the pressure inside the sucking region 14b is kept to be negative. The suction duct 21 and the sucking device 24 constitute a sucking means 31. This sucking means 31 will be described later.

In the structure above, when the air in each of the sucking region 14a and the sucking region 14b is sucked through the suction duct 21 so that the pressures inside the sucking region 14a and the sucking region 14b are kept to be negative, an air flow from the outer circumference side of the adsorbent molding section 12a toward the inside of the cylinder 12 is generated in the duct 4 having the other-end-side opening 4c that opposes the two sucking regions 14a and 14b. By this air flow, the mixed flow of the fluff pulp and the water absorbing polymer is carried by air in the duct 4 toward the rotating fiber stacking drum 7.

It is noted that, in accordance with the length of the absorbent body to be formed (i.e., the circumferential length of the adsorbent molding section 12a), the inside of one or both of the sucking region 14a and the sucking region 14b is arranged to be negative in pressure. That is to say, when the absorbent body to be formed is relatively short, the inside of one of the sucking region 14a and the sucking region 14b is arranged to be negative in pressure. On the other hand, when the absorbent body to be formed is relatively long, the inside of the sucking region 14a and the inside of the sucking region 14b are both arranged to be negative in pressure. In this way, the absorbent body with the desired length is formed.

In addition to the above, to the discharge region 14c, one end of the air supply duct 22 which has the other end connected to an air supplier 25 (shown in FIG. 2) such as a compressor is connected. As the air supplier 25 supplies compressed air into the discharge region 14c through the air supply duct 22, the inside of the discharge region 14c is arranged to be positive in pressure. The air supply duct 22 and the air supplier 25 constitute a supplying means 32. This supplying means 32 will be described later.

In addition to the above, in the discharge region 14c, a discharge guide 23 is provided to guide the compressed air in such a way that the compressed air in the discharge region 14c is discharged from the inside of the cylinder 12 to the outer circumference side of the adsorbent molding section 12a. This discharge guide 23 is formed to be U-shaped in cross section and open only downward in the figure, in order to guide the compressed air toward the vacuum conveyor 8.

The other end of the air supply duct 22 penetrates an opening of the side wall 11 and is connected to a side-wall opening of the discharge guide 23. In this way, the air supply duct 22 is connected to the inside of the discharge guide 23. The width of the discharge guide 23 (i.e., the length in the direction orthogonal to the plane of the figure) is arranged to be longer than the width of the adsorbent molding section 12a.

In this structure, as the compressed air is supplied into the discharge region 14c through the air supply duct 22 and hence the inside of the discharge region 14c becomes positive in pressure, the compressed air guided to the discharge guide 23 is discharged from the inside of the cylinder 12 to the outer circumference side of the adsorbent molding section 12a. In other words, the compressed air guided to the discharge guide 23 is discharged toward the vacuum conveyor 8 that opposes the discharge region 14c.

On account of a pressing force of this compressed air and a later-described sucking force of the vacuum conveyor 8, the absorbent body in the adsorbent molding section 12a is passed to the vacuum conveyor 8.

The vacuum conveyor 8 contacts with a part of the rotating fiber stacking drum 7 via amount (not illustrated) which is provided for supporting the absorbent body. The vacuum conveyor 8 is provided with a sucking device (not illustrated) generating a sucking force, at a part of the inside of the vacuum conveyor 8 which part opposes a part contacting with the rotating fiber stacking drum 7. The absorbent body formed at the adsorbent molding section 12a of the cylinder 12 of the rotating fiber stacking drum 7 is passed to the surface of the mount by the pressing force of the compressed air discharged toward the vacuum conveyor 8 and the sucking force of the vacuum conveyor 8.

(Sucking Means)

Figure 2:
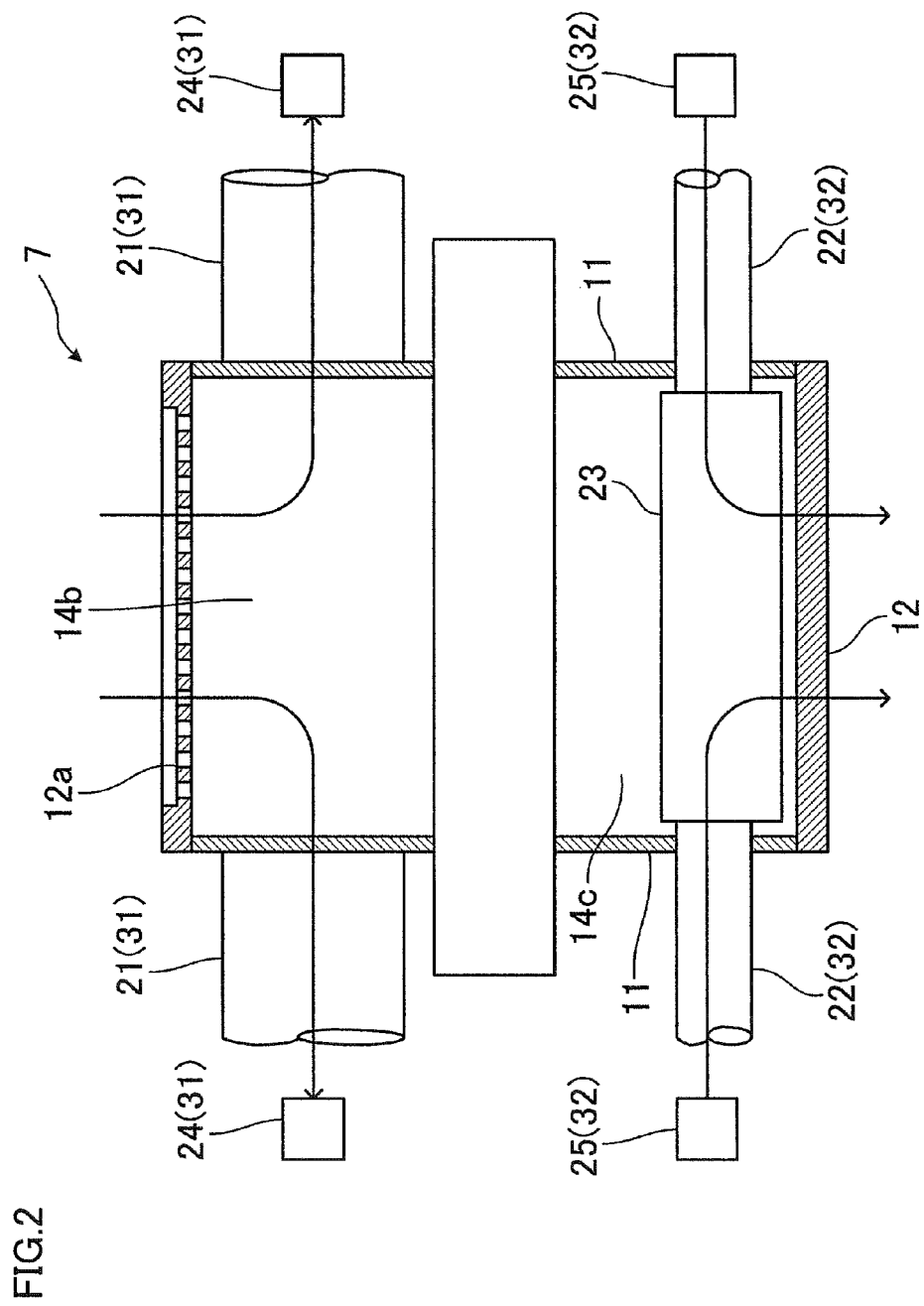
FIG. 2 is a cross section taken at the A-A line in FIG. 1.

As shown in FIG. 2 which is a cross section taken at the A-A line in FIG. 1, the sucking means 31 includes the suction duct 21 connected to the sucking region 14b and the sucking device 24 which is configured to suck the air in the sucking region 14b through the suction duct 21. For the sucking region 14a, a similar sucking means 31 is provided. The sucking device 24 is provided outside of the rotating fiber stacking drum 7 so as not to be rotatable. One end of the suction duct 21 is connected to the sucking device 24, whereas the other end of the suction duct 21 is connected to an opening formed through the side wall 11 of the rotating fiber stacking drum 7.

In the present embodiment, the sucking means 31 connected to the sucking region 14b is provided on each of the one end side and the other end side of the rotating fiber stacking drum 7 in the axis direction. The suction duct 21 of the sucking means 31 is connected to each of the two side walls 11 of the rotating fiber stacking drum 7. The same holds true for the sucking region 14a.

If the sucking means 31 is connected only to one side wall 11 of the rotating fiber stacking drum 7, assuming that the axis direction of the rotating fiber stacking drum 7 is a width direction, the sucking force on the side of the side wall 11 to which the sucking means 31 is connected is relatively larger than the sucking force on the other side wall 11 side when a wide absorbent body is formed. Because the sucking force is uneven in the width direction of the adsorbent molding section 12a, the thickness of the absorbent body molded by the adsorbent molding section 12a is disadvantageously uneven in the width direction.

In this regard, the air in the rotating fiber stacking drum 7 (sucking regions 14a and 14b) is sucked by the sucking means 31 connected to the respective two side walls 11 of the rotating fiber stacking drum 7. With this, the sucking force is uniform in the width direction of the adsorbent molding section 12a, even when a wide absorbent body is formed. As a result, the thickness of the absorbent body molded by the adsorbent molding section 12a is made uniform in the width direction.

Furthermore, because the paired side walls 11 do not rotate with respect to the rotating cylinder 12, it is possible to easily connect the suction ducts 21 to the respective side walls 11.

(Supplying Means)

In addition to the above, as shown in FIG. 2, the supplying means 32 includes the air supply duct 22 connected to the discharge guide 23 in the discharge region 14c and the air supplier 25 configured to supply compressed air into the discharge guide 23 through the air supply duct 22. The air supplier 25 is provided outside the rotating fiber stacking drum 7 so as not to be rotatable. One end of the air supply duct 22 is connected to the air supplier 25, whereas the other end of the air supply duct 22 penetrates an opening formed through the side wall 11 of the rotating fiber stacking drum 7 and is connected to a side wall opening of the discharge guide 23.

In the present embodiment, the supplying means 32 are provided on the one end side and the other end side of the rotating fiber stacking drum 7 in the axis direction, respectively. The air supply ducts 22 of the supplying means 32 are connected to the respective two side walls 11 of the rotating fiber stacking drum 7.

Provided that the supplying means 32 is connected only to one side wall 11 of the rotating fiber stacking drum 7, the pressing force on the side wall 11 side where the supplying means 32 is connected is relatively larger than the pressing force on the opposite side wall 11 side in an attempt to take a wide absorbent body out from the adsorbent molding section 12a by means of a pressing force of compressed air. As such, the pressing force is not uniform in the width direction of the adsorbent molding section 12a, with the result that the absorbent body cannot be successfully taken out from the adsorbent molding section 12a.

In this regard, the supplying means 32 are connected to the respective two side walls 11 of the rotating fiber stacking drum 7 to supply the compressed air into the discharge region 14c from the both sides. With this arrangement, a pressing force which is uniform in the width direction of the adsorbent molding section 12a is exerted even if a wide absorbent body is formed. In this way, the absorbent body is successfully taken out from the adsorbent molding section 12a.

(Effects)

As described above, in the device 1 for producing the absorbent body of the present embodiment, because the air in the rotating fiber stacking drum 7 (sucking regions 14a and 14b) is sucked by the sucking means 31 connected to the respective two side walls 11 of the rotating fiber stacking drum 7, a sucking force which is uniform in the width direction of the adsorbent molding section 12a is exerted even when a wide absorbent body is formed. As a result, the thickness of the absorbent body molded by the adsorbent molding section 12a is made uniform in the width direction.

In addition to the above, because the paired side walls 11 do not rotate with respect to the rotating cylinder 12, it is possible to easily connect the sucking means 31 to the paired side walls 11, respectively.

Furthermore, because the supplying means 32 are connected to the respective two side walls 11 of the rotating fiber stacking drum 7 to supply compressed air into the discharge region 14c, the pressing force is uniform in the width direction of the adsorbent molding section 12a even if a wide absorbent body is formed. This makes it possible to successfully take the absorbent body out from the adsorbent molding section 12a.

(Modifications of Present Embodiment)

The above embodiment thus described solely serves as a specific example of the present invention, and the present invention is not limited to such an example. Specific structures of various means and the like may be suitably designed or modified. Further, the effects of the present invention described in the above embodiment are not more than examples of most preferable effects achievable by the present invention. The effects of the present invention are not limited to those described in the embodiments described above.

For example, as indicated by the dotted lines in FIG. 1, the suction duct 21 may be sufficiently separated from the other-end-side opening 4b of the duct 4. This further uniformizes the air flow passing the adsorbent molding section 12a, as compared to the case where the suction duct 21 is close to the other-end-side opening 4b.

REFERENCE SIGNS LIST

1: DEVICE FOR PRODUCING ABSORBENT BODY
3: CRUSHER
3a: ROTATING BLADE
4: DUCT
4a: ONE-END-SIDE OPENING
4b: OTHER-END-SIDE OPENING
7: ROTATING FIBER STACKING DRUM
8: VACUUM CONVEYOR
11: SIDE WALL
12: CYLINDER
12a: ADSORBENT MOLDING SECTION
13: PARTITION PLATE
14a, 14b: SUCKING REGION
14c: DISCHARGE REGION
21: SUCTION DUCT
22: AIR SUPPLY DUCT
23: DISCHARGE GUIDE
24: SUCKING DEVICE
25: AIR SUPPLIER
31: SUCKING MEANS
32: SUPPLYING MEANS

The invention claimed is:

1. A device for producing an absorbent body, comprising:
a rotating fiber stacking drum that includes an adsorbent molding section configured to mold fluff pulp into an absorbent body having a desired shape, the rotating fiber stacking drum including:
a cylinder having an outer circumference on which the adsorbent molding section is formed; and
paired side walls that close ends of the cylinder, respectively,
the device further comprising:
a partitioning plate partitioning the inside of the rotating fiber stacking drum into plural regions including a sucking region and a discharge region;
paired sucking means, which are connected with the paired side walls, respectively, to communicate with the sucking region and are configured to generate an air flow from the outer circumference side of the adsorbent molding section toward the inside of the cylinder by sucking air in the sucking region;
paired supplying means which are connected with the paired side walls, respectively, to communicate with the discharge region and supply compressed air into the discharge region; and
a discharge guide which is provided in the discharge region, is U-shaped in cross section to be open toward the outer circumference side of the adsorbent molding section, and guides the compressed air to be discharged from the inside of the cylinder toward the outer circumference side of the adsorbent molding section.

2. The device according to claim 1, wherein:
the paired side walls are arranged not to be rotatable, and the cylinder is arranged to be rotatable.

* * * * *